United States Patent
Fellowes et al.

(10) Patent No.: US 11,133,088 B2
(45) Date of Patent: Sep. 28, 2021

(54) RESOLVING CONFLICTING DATA AMONG DATA OBJECTS ASSOCIATED WITH A COMMON ENTITY

(71) Applicant: International Business Machines Corporation, Armonk, NY (US)

(72) Inventors: Peter A. Fellowes, Cleveland, OH (US); Jacob O. Miller, Cleveland, OH (US); Matthew M. Pohlman, University Heights, OH (US)

(73) Assignee: International Business Machines Corporation, Armonk, NY (US)

( * ) Notice: Subject to any disclaimer, the term of this patent is extended or adjusted under 35 U.S.C. 154(b) by 750 days.

(21) Appl. No.: 15/355,186

(22) Filed: Nov. 18, 2016

(65) Prior Publication Data

US 2018/0144095 A1    May 24, 2018

(51) Int. Cl.
*G16H 10/60* (2018.01)
*G16H 50/20* (2018.01)
*G16H 40/67* (2018.01)

(52) U.S. Cl.
CPC ............. *G16H 10/60* (2018.01); *G16H 40/67* (2018.01); *G16H 50/20* (2018.01)

(58) Field of Classification Search
CPC ......... G16H 10/60; G16H 40/67; G16H 50/20
USPC .......................................................... 705/3
See application file for complete search history.

(56) References Cited

U.S. PATENT DOCUMENTS

| | | |
|---|---|---|
| 8,364,499 B2 | 1/2013 | Maughan et al. |
| 8,990,834 B2 | 3/2015 | Mathur et al. |
| 2002/0120472 A1* | 8/2002 | Dvorak ................. G06Q 50/24 705/3 |
| 2003/0177132 A1* | 9/2003 | Thomas ................ G06Q 10/10 |
| 2003/0220821 A1 | 11/2003 | Walter et al. |
| 2004/0172221 A1* | 9/2004 | Curry, II ............ G06F 11/0751 702/186 |
| 2005/0071194 A1* | 3/2005 | Bormann ............... G06Q 50/22 705/2 |

(Continued)

OTHER PUBLICATIONS

Robert C. Paule and John Mandel, "Consensus Values and Weighting Factors", Journal of Research of the National Bureau of Standards, vol. 87, No. 5, Sep.-Oct. 1982, pp. 377-438 (Year: 1982).*

(Continued)

*Primary Examiner* — Jonathan Durant
*Assistant Examiner* — Joshua B Blanchette
(74) *Attorney, Agent, or Firm* — Will Stock; Edell, Shapiro & Finnan, LLC

(57) ABSTRACT

Resolving conflicting data among data objects associated with a common entity includes assigning an ordered sequence of data analysis processes to a corresponding data field of a plurality of data objects associated with a common entity. At least two of the data objects include different values for the corresponding data field, and each data analysis process performs a different technique to resolve conflicts between different values of data. The ordered sequence of data analysis processes is executed to determine a consensus value to serve as a value for the corresponding data field of each of the plurality of data objects. The data analysis processes are successively executed in the ordered sequence until the consensus value is determined for the corresponding data field.

17 Claims, 9 Drawing Sheets

(56) References Cited

U.S. PATENT DOCUMENTS

| | | | | |
|---|---|---|---|---|
| 2008/0147436 A1* | 6/2008 | Ohlsson | ............... | G06Q 10/087 |
| | | | | 705/2 |
| 2008/0288023 A1 | 11/2008 | John | | |
| 2009/0228303 A1* | 9/2009 | Faulkner | ................ | G06Q 50/22 |
| | | | | 705/3 |
| 2010/0042433 A1* | 2/2010 | Schneider | .............. | G06Q 50/22 |
| | | | | 705/3 |
| 2010/0114951 A1* | 5/2010 | Bauman | .................. | G06F 16/13 |
| | | | | 707/770 |
| 2012/0005527 A1* | 1/2012 | Engel | ..................... | H04H 60/64 |
| | | | | 714/15 |
| 2012/0060216 A1* | 3/2012 | Chaudhri | ............... | G16H 70/00 |
| | | | | 726/21 |
| 2012/0101849 A1* | 4/2012 | Mathur | ................. | G06F 19/328 |
| | | | | 705/3 |
| 2013/0080192 A1* | 3/2013 | Bucur | .................... | G06Q 50/24 |
| | | | | 705/3 |
| 2013/0110525 A1 | 5/2013 | Whittier et al. | | |
| 2014/0032240 A1 | 1/2014 | Lougheed et al. | | |
| 2014/0214450 A1* | 7/2014 | Bechtold | ............... | G16H 10/60 |
| | | | | 705/3 |
| 2017/0270626 A1* | 9/2017 | Koll | ....................... | G06Q 10/10 |

OTHER PUBLICATIONS

"The Explorys Platform", IBM Watson Health, Solution Brief, Produced in the United States of America, Nov. 2015, 4 pages.

* cited by examiner

RESOLVING CONFLICTING DATA AMONG DATA OBJECTS ASSOCIATED WITH A COMMON ENTITY

BACKGROUND

1. Technical Field

Present invention embodiments relate to data matching systems, and more specifically, to resolving conflicts between data that has been matched with a common entity by a matching system, such as a matching system for healthcare data.

2. Discussion of the Related Art

Healthcare networks have very complicated organization structures. An organization typically comprises multiple source systems (e.g., a source of electronic medical records including electronic health records (EHR), records from a claims system, lab feed, various data sources implementing the HL7 standard, patient satisfaction survey, etc.). Within each source system, data may be input for various entities (i.e., patients, companies, etc.), perhaps based on forms that a patient fills out. Accordingly, various data objects in a source system may be associated with a common entity (i.e., patients) even though the data objects have different information contained therein. For example, data objects within different source systems of an organization or even within a single source system of a single organization may be associated with a common patient.

Matching algorithms often determine when these data objects are associated with a common patient, but if the information (e.g., demographic information) included in the data objects differs, the matching algorithms may create a patient with mismatched information. Consequently, queries performed against records associated with a common patient may return confusing or inaccurate results. These problems become exacerbated as data is shared across clinically integrated networks (CIN) or galaxies (e.g., a group of organizations), instead of just source systems within an organization. Examining underlying records of different source systems, let alone different healthcare systems, to try to resolve conflicts between data records associated with a common patient may be complex, burdensome, and processing intensive (in terms of resources and time).

SUMMARY

According to one embodiment of the present invention, resolving conflicting data among data objects associated with a common entity includes assigning an ordered sequence of data analysis processes to a corresponding data field of a plurality of data objects associated with a common entity. At least two of the data objects include different values for the corresponding data field, and each data analysis process performs a different technique to resolve conflicts between different values of data. The ordered sequence of data analysis processes is executed to determine a consensus value to serve as a value for the corresponding data field of each of the plurality of data objects. The data analysis processes are successively executed in the ordered sequence until the consensus value is determined for the corresponding data field.

BRIEF DESCRIPTION OF THE DRAWINGS

Generally, like reference numerals in the various figures are utilized to designate like components.

DETAILED DESCRIPTION

Figure 1:
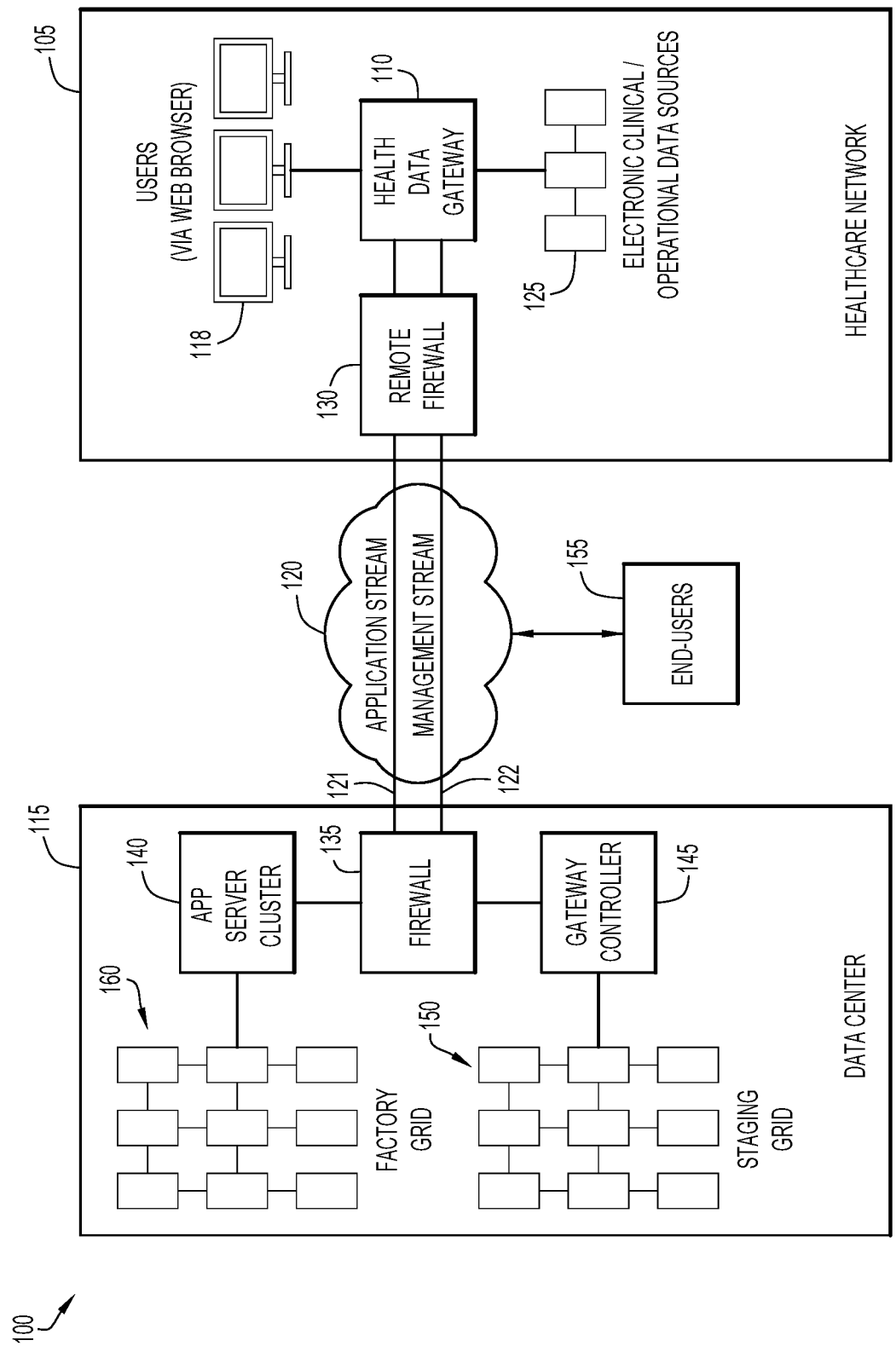
FIG. 1 is a diagrammatic illustration of an example computing environment according to an embodiment of the present invention.

An organization may comprise multiple source systems (e.g., a source of electronic medical records including electronic health records (EHR), records from a claims system, lab feed, various data sources implementing the HL7 standard, patient satisfaction survey, etc.), while clinically integrated networks (CIN) or galaxies (e.g., a group of organizations) are collections of individual healthcare systems with data sharing agreements. Present invention embodiments primarily pertain to resolving conflicting data among data records (e.g., patient or other entity records) that are or have been matched at a source system or organizational level. However, in some embodiments, present invention embodiments could be used to resolve conflicts between entity matches within a galaxy, or entity matches between galaxies, if desired. Regardless, this conflict resolution may accurately determine the identity of an entity (e.g., patient) by identifying the most accurate demographic information.

Present invention embodiments provide several advantages. Generally, present invention embodiments support or improve data management and collaboration within a medical organization and/or between medical organizations. Present invention embodiments may increase the accuracy and quality of data that is available to medical professionals and/or generate new data with higher quality and accuracy than existing records, thereby improving medical care and diagnoses. Moreover, resolving conflicts between data objects with an iterative application of various data analysis processes may allow conflicts for different fields to be resolved with processes that are most accurate for that particular field. Increasing the effectiveness and accuracy of these processes may, in turn, support complex data governance issues of an organization, galaxy, or across galaxies.

As examples of more specific advantages, present invention embodiments allow demographic records to be compared across source systems, organizations, and galaxies. The comparisons eliminate errors, such as typographical errors, and may create a new demographic record that includes only the most recent demographic information for a particular person. Consequently, any analytical processing performed on the new demographic records generated by present invention embodiments will efficiently return accurate results (e.g., because the processed demographic records include a single instance of accurate results). In other words, present invention embodiments improve analytical processing of demographic records.

Furthermore, in at least some embodiments, the comparisons can be performed without querying external (e.g., third-party) databases, without clinician verification (e.g., in at least some embodiments, a nurse or doctor is not required to verify a consensus value that is determined or generated for a particular field), and/or without checking any test results. At the very least, the comparisons are performed without consulting external records for the entity in question (e.g., the patient), thereby providing increased security and anonymity as compared to solutions that require verification from external records for a common entity. Instead, ambiguities are resolved statistically, possibly with reference to publicly available data records. Still further, present invention embodiments resolve conflicts on a field by field basis, applying field-specific analyses to each field to resolve a conflict. This provides a modularity that allows the logic behind each individual analytical process and/or the series of processes applied to a particular field to be easily changed or updated.

As yet another example advantage, present invention embodiments produce a new record for a particular entity once consensus values have been determined for each field associated with the entity. The new record includes an indication of the data analysis processes and the source records used to generate each consensus value included in the new record. This provides historical context when investigating performance or matching to a new record (e.g., for debugging and/or tracking). Moreover, when the new record is created, the source records are left unchanged and, thus, the data integrity of the source records is not negatively impacted.

The conflict resolution is preferably implemented in a distributed computing environment, as described below, and is highly scalable. By way of example, millions of source records may be processed in a short time interval (e.g., minutes) since conflict resolution is performed for a single patient or entity with a relatively small quantity of records. However, present invention embodiments are environment agnostic and may also be implemented in non-distributed computing environments if desired.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
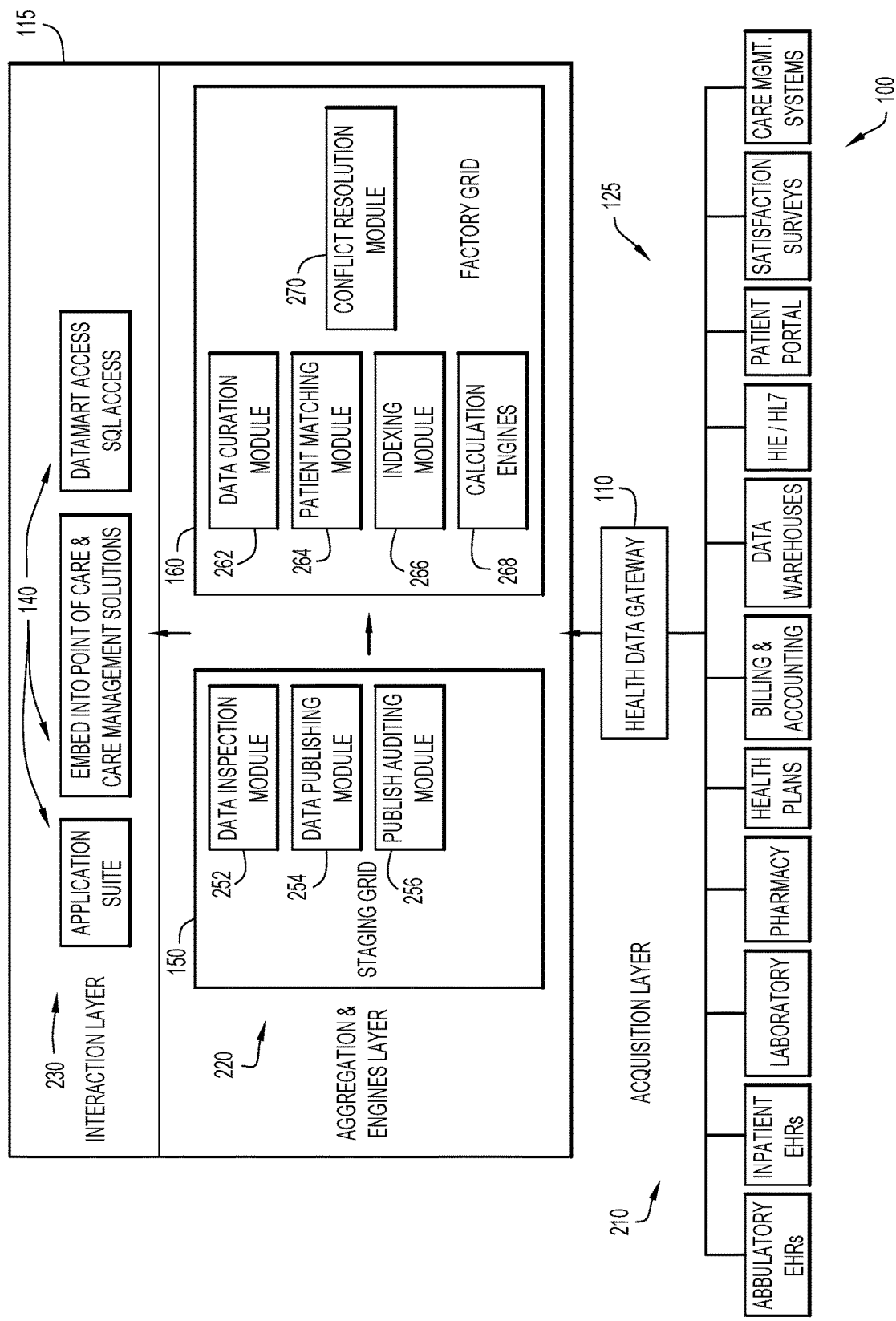
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, various calculation/analytic engines 268, and a conflict resolution module 270. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines 268 perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer. The conflict resolution module 270 performs operations to determine a consensus value for conflicting data fields of patient records associated with the same patient (e.g., as determined by patient matching module 264).

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
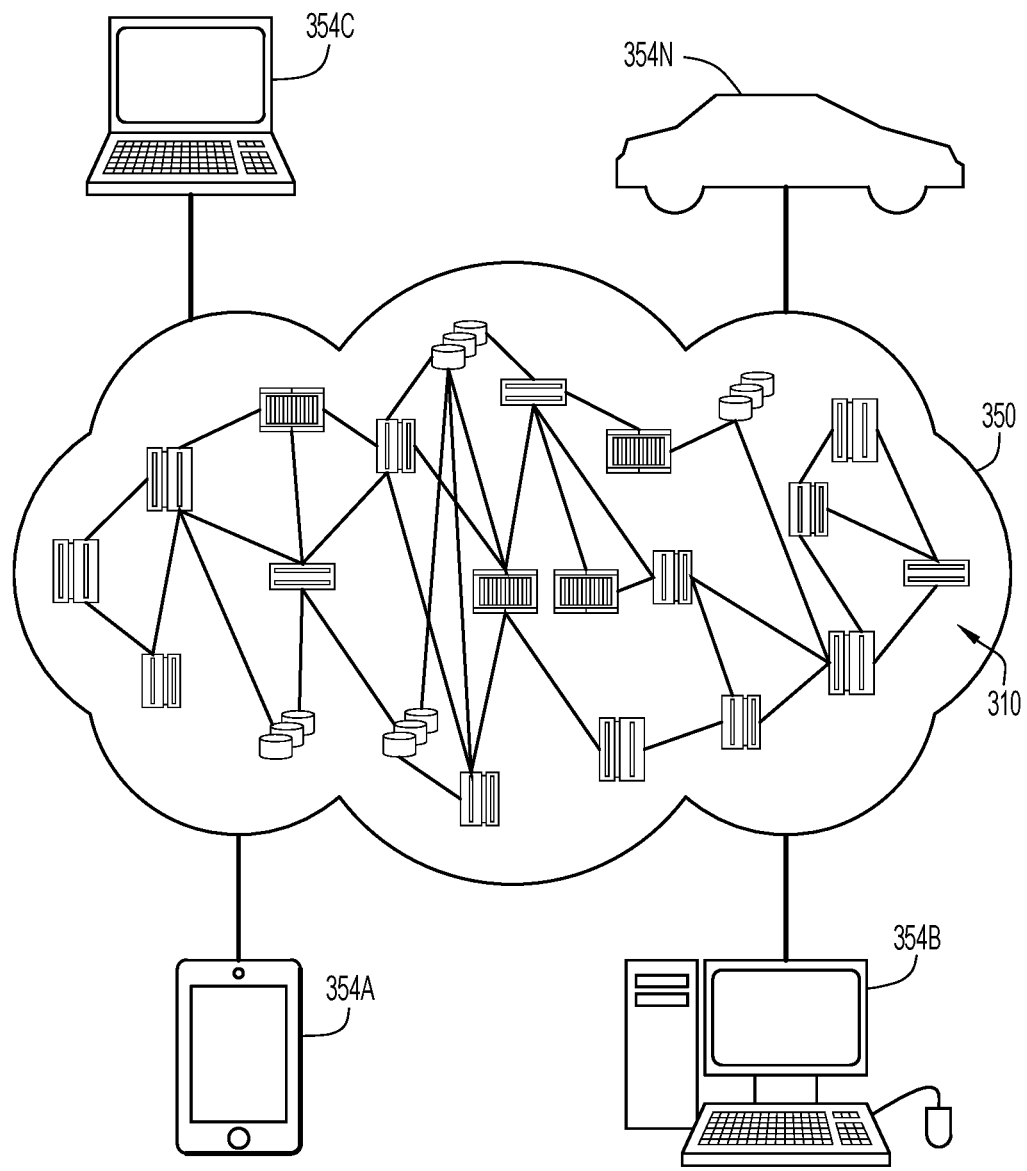
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
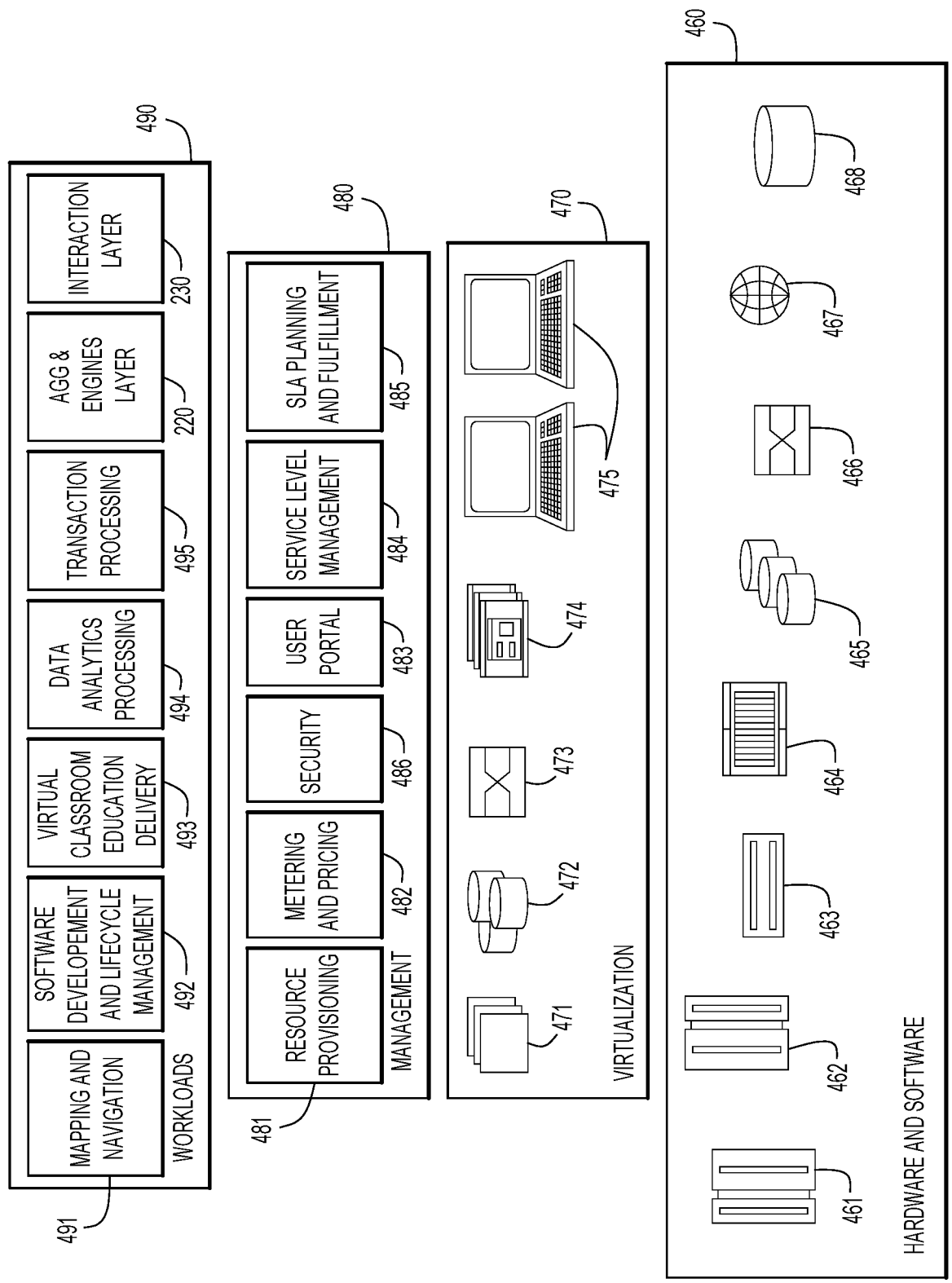
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
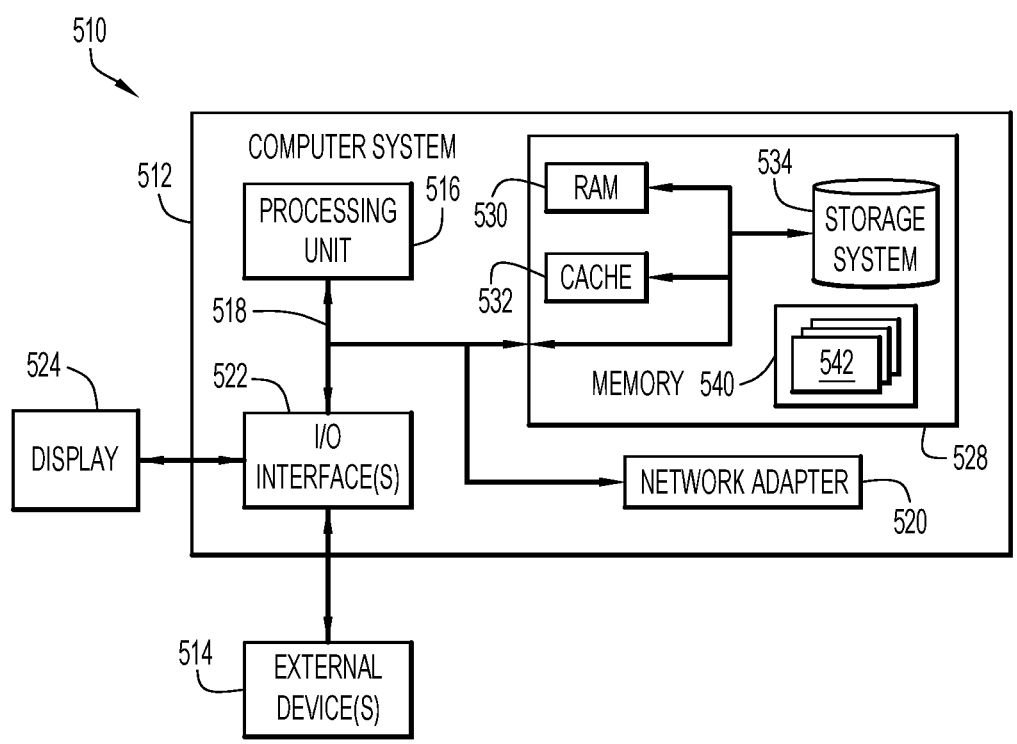
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

In FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
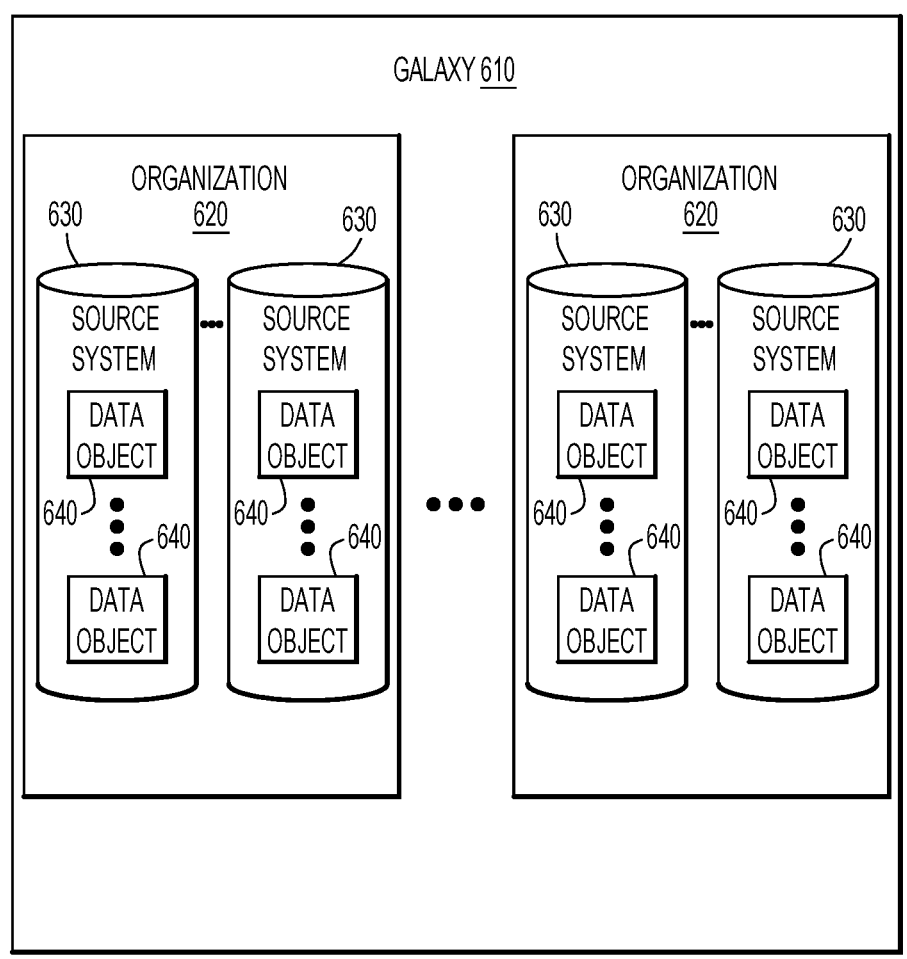
FIG. 6 is a block diagram illustrating the organization of data objects in a healthcare computing system according to an embodiment of the present invention.

FIG. 6 illustrates an example organization of data objects in a healthcare computing system, according to an embodiment of the present invention. As shown, data objects 640 may be distributed within a source system 630 of an organization 620 (which may, in turn, be part of a galaxy 610). For example, each source system 630 contains medical or other records associated with patients and events and, in particular, data generated by or during human interactions regarding healthcare events (e.g., source systems 630 may correspond to source systems 125 described above in connection with FIG. 2). However, source systems 630 may contain any types of records, and the system may analyze records associated with any type of desired entity (e.g., person, corporate or other business entity, healthcare or other medical related entity, healthcare provider, etc.) in substantially the same manner described below (e.g., to resolve conflicts).

Figure 7:
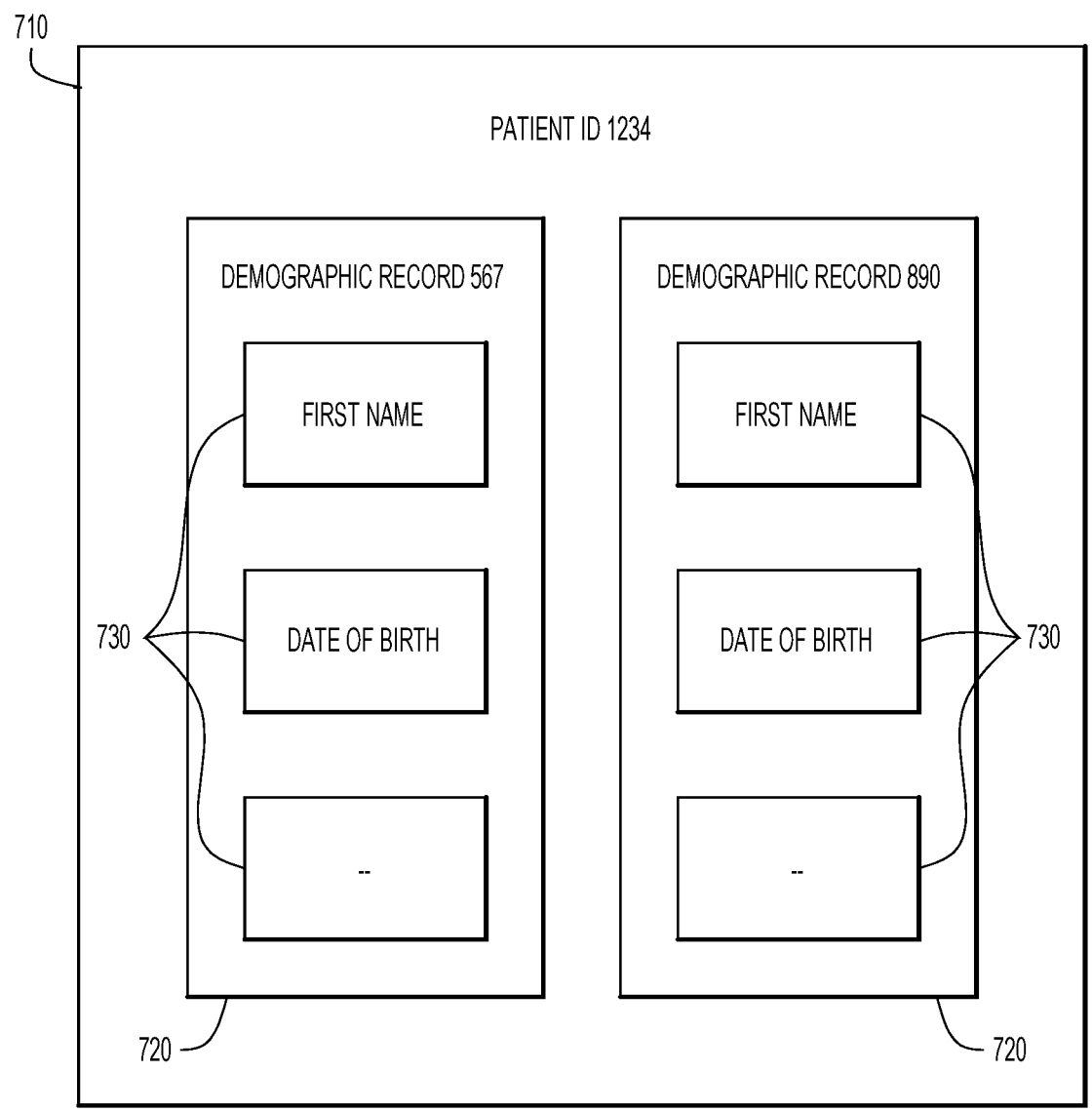
FIG. 7 is a block diagram illustrating the organization of data in a data record associated with a common entity according to an embodiment of the present invention.

In FIG. 7, an example organization of data associated with a common entity 710, such as a patient identifier (ID) 1234, is illustrated in order to illustrate one level at which conflicts may be resolved by present invention embodiments. Generally, one or more matched demographic records 720 (e.g., records matched by various matching algorithms analyzing records from various source systems 630 in an organization 620) are associated with a common entity 710. More specifically, in the depicted embodiment, at least two demographic records 720 (record 567 and record 890) have been determined to be associated with a common patient ID 1234 using various patient matching techniques, such as Probabilistic Patient Matching (PPM).

In different embodiments, a record 720 may include any number of fields 730. In some instances, different records 720 may include different fields, but demographic or patient records also typically include several identical fields 730, such as name, birthdate, gender, and address (though the values in each field may not be identical to the value of the same field in another record). Often, patient matching techniques, such as PPM, match demographic records 720 together under a single patient ID 710 when the demographic records 720 have similar fields 730 and, thus, are likely to represent the same person. In most cases, the fields 730 included in the demographic records 720 of a matched set of patient records 710 will match; however, there are still many instances where the fields 730 do not provide an exact match (for example, a typo in a name may be present in one record). In other words, in at least some instances, demographic records 720 associated with a common entity (e.g., demographic records included in a set of matched records) may include conflicting data values for the same field 730.

Figure 8:
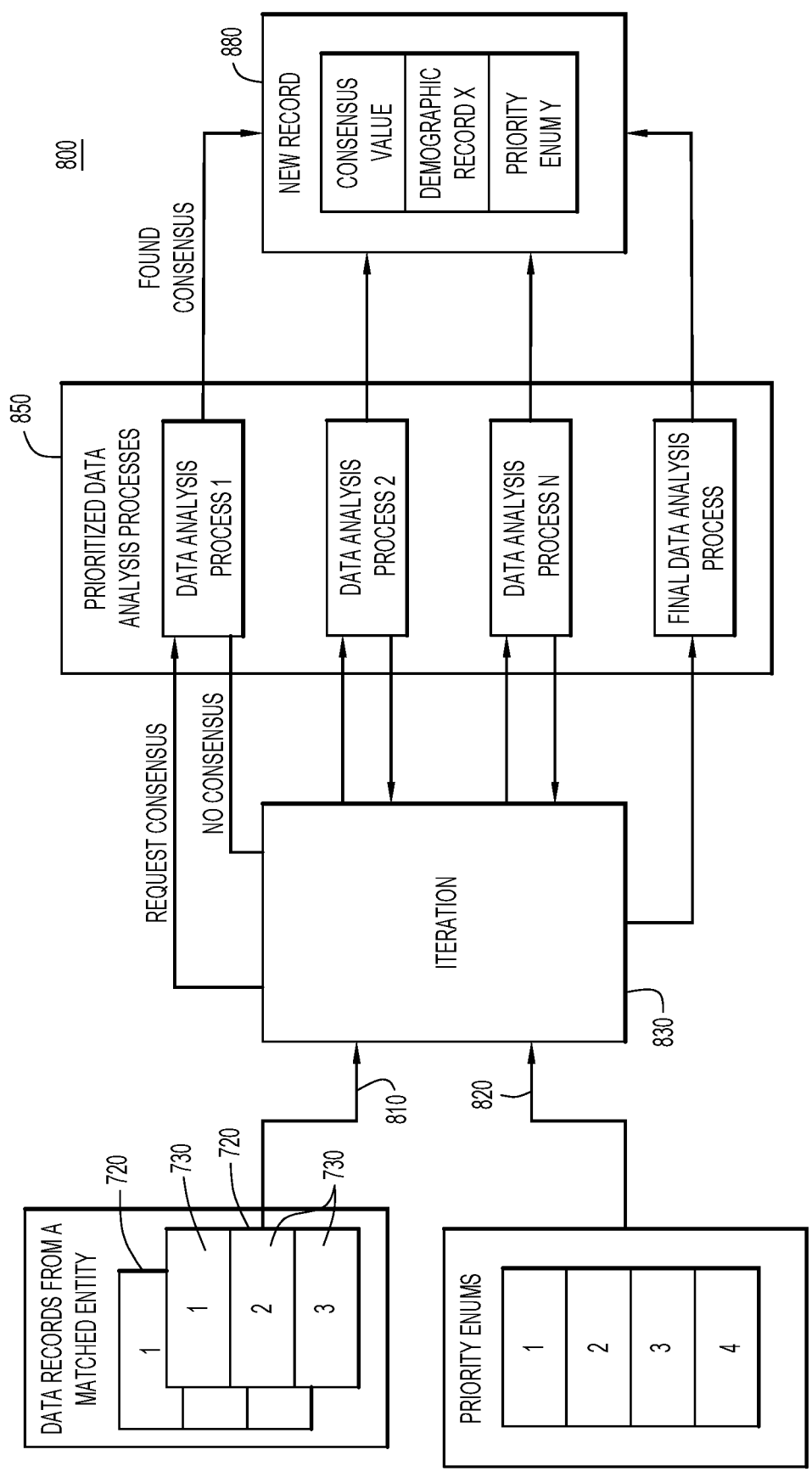
FIG. 8 is a diagrammatic illustration of a manner of resolving conflicts within data fields of data records associated with a common entity, according to an embodiment of the present invention.
Figure 9:
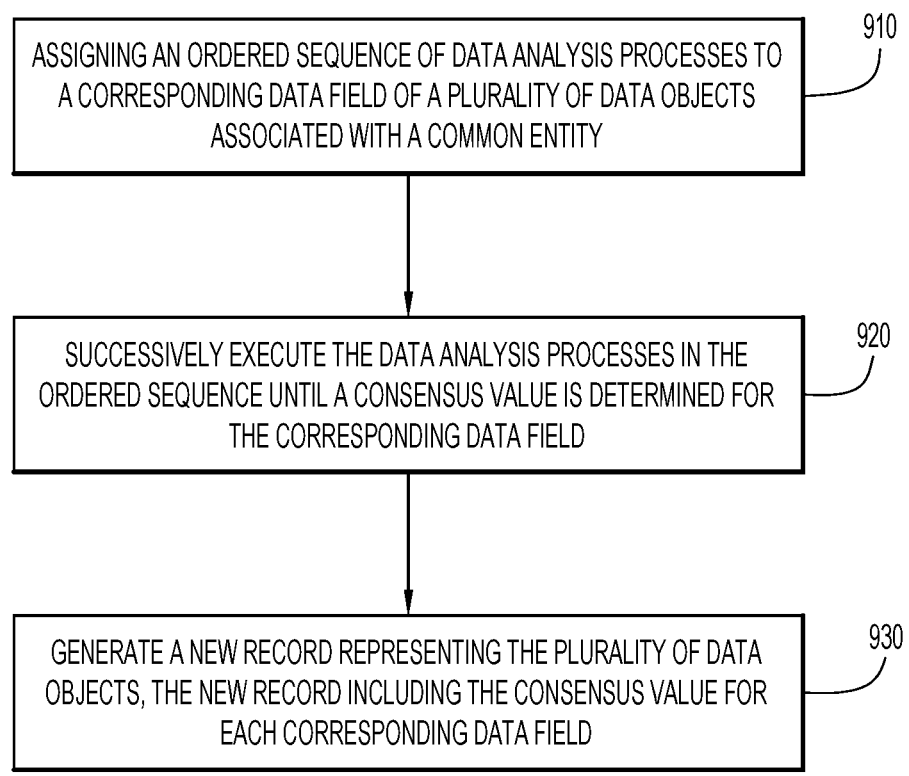
FIG. 9 is a procedural flowchart illustrating a manner of resolving conflicts within data fields of data records associated with a common entity, according to an embodiment of the present invention.

A manner of resolving conflicting data among data objects associated with a common entity (e.g., via the factory grid and conflict resolution module 270), is illustrated in FIGS. 8 and 9. In these particular examples, the conflicts exists between data for at least one particular field 730 of two patient records 720 associated with the same common entity 710, however, in other embodiments, conflicts may be resolved between any desirable data of matched data objects. Generally, these techniques determine a consensus value for non-matching fields, insofar as the consensus value is the value that it most likely to be correct for a particular field and generate a new record including the consensus value for each field (the techniques may also determine a consensus in cases where data objects all match to ensure the new record is complete). In some instances, the consensus value may resolve a conflict between standardized and unstandardized values, however, the consensus value does not simply standardize data, it resolves conflicts between different data values by determining the value most likely to be accurate.

FIG. 8 provides a block diagram 800 illustrating steps associated with resolving conflicting data, according to an example embodiment. At a high level, the steps iterate through the various fields included in records associated with a common entity (e.g., records 720) to resolve conflicts in each field (e.g., fields 730). To resolve the conflicts included in a particular field of the records associated with the common entity, data analysis processes are executed in a priority order that is determined based on the particular field being analyzed.

More specifically, the data records associated with a matched entity are retrieved or received at 810. Then, at 830, the algorithm begins to iterate through the fields 730 (indicated as 1, 2, and 3 in FIG. 8) included in the records 720 from the matched entity. The algorithm also receives or retrieves, at 820, an array of priority enums (constants) that correspond to a data analysis process to call later. The order of the enums is determined based on a priority order that is associated with the particular field being evaluated and the order of the enums in the array determines the order in which the data analysis processes are called. Each field 730 has a corresponding priority order, and many share the same priority order. The array of enums and the priority orders of particular fields define an order of data analysis processes to be executed against data values included in the data fields 730 of the records 720 associated with the common entity 710.

Consequently, at 830, for each field 730, the enums are iterated through in the particular priority order associated with a particular field. For each enum, the iteration passes the data values for the field being processed (and records) to the data analysis process called by the enum. As is explained in further detail below, in at least some embodiments, either all versions of a field are in agreement, and a consensus does not need to be reached (e.g., no conflict is present), or there is disagreement, and a consensus value must be identified. When a consensus value needs to be identified, a first data analysis process analyzes the data values through one of various data analysis processes, such as probabilistic estimates based on frequency of co-occurrences of various values across fields, and attempts to determine a consensus value. If the first data analysis process determines or generates a consensus value, a new field is generated in a new record at 880. If not, the next data analysis process attempts to determine or generate a consensus value for the particular field.

Various data analysis processes continue to be executed in attempt to find a consensus value until a final data analysis process is reached, at which point the final data analysis must find a consensus value. Whenever a consensus value is generated by a data analysis process, a new field is generated. The new field includes the determined/generated consensus value, the source record (e.g., the record 720 that the consensus value was taken from (if any)), and the data analysis process used to determine the consensus value. Moreover, once a consensus value has been found for a particular field 730 of the records 720 associated with the common entity 710, the iteration moves to the next field of the records 720 and attempts to determine a consensus value by executing various data analysis processes in a priority order particular to that specific field. Once the algorithm has performed this process for each of the fields of the common entity, the algorithm may retrieve data records associated with another common entity (e.g., another patient) and repeat the same steps.

As a more specific example, in at least one embodiment, at least six types of data analysis processes may be implemented and any number of these data analysis processes may be assigned to different fields in different priority orders. The data analysis processes may include the following processes: a no conflict analysis process, a plurality analysis process, a preferred record analysis process, an aggregate analysis process, a newest analysis process, and a field-specific analysis processes (e.g., a gender analysis process or a birth date analysis process).

The no conflict analysis process may designate any data value for a field as the consensus value when there is no ambiguity between the data of the particular field across the data records for the common entity. For example, if all data records indicate that a particular patient has a first name of Taylor; Taylor may be designated as the consensus value for the first name field.

The plurality analysis process may count the number of instances of each data entry for a particular field, such as by generating a hash map for a particular field and incrementing the count for each data value based on the entries in the hash map. With this data analysis process, if a particular data value outnumbers all other data values, the particular data value will be designated as the consensus value. For example, consider a scenario where the data records for a particular patient include the following data values for the first name field: four instances of John, one instance of Jon, and one instance of Joan. In this scenario, John may be determined to be the consensus value using the plurality analysis process because four instances is the highest number of instances of any particular data value.

In different embodiments, the plurality analysis process may be required to satisfy a threshold in order to designate a particular data value as the consensus value. For example, in some embodiments, a particular data value must have a count that is at least 50% higher than the next most frequent data value (e.g., the data value with the second highest count) to be designated as the consensus value. In some embodiments, the threshold may be a predetermined threshold that is applied across all fields, but in other embodiments, the threshold may vary based on the field, the data source of the source records being evaluated, or any other criteria. For example, if a source system is known to keep multiple copies of data, the threshold may be increased to ensure that a single source system does not improperly skew the plurality counts.

The preferred record analysis process may determine a consensus value by consulting a list of source system preferences. The list may be received from a user, in any form, or created based on a known or determined quality of the source systems hosting the data records under evaluation. For example, in some embodiments, billing systems may be designated as low quality source systems because billing systems only include data from a snapshot in time, while electronic medical record (EMR) source systems may be designated as high quality source systems and, thus, records from EMR source systems may be prioritized over records from a billing system on a priority list. Regardless of how the priority list is obtained, when data values for a particular field are evaluated with the preferred record analysis process, the data value from a record highest on the priority list may be designated as the consensus value.

The aggregate data analysis process may create a consensus value by aggregating all conflicting data values together and filtering any duplicate values. In other words, this data analysis process generates a consensus value by building a new list or set that includes all data values included in a particular field of the records associated with a common entity. As is discussed in further detail below, this data analysis processes may be particularly suited to data fields that may properly include more than one data value, such as a fields that are lists or sets (as opposed to fields that are likely to only have one correct answer, such as birthdate).

The newest data analysis process selects a consensus value based on which data value has been most recently created or updated. In some embodiments, the conflicting data values will be evaluated to determine which data value was most recently created or updated. However, in other embodiments, the analysis process may select the data value from the data record that has been updated or created most recently (since any update to a record may be most likely to include up-to-date information). As is explained in further detail below, this data analysis process may be particularly useful for evaluating demographic information that is expected to change, such as address, phone, email, last name (particularly for females), etc.

The field specific data analysis processes may apply a data analysis process that is particularly suited for data values included in a particular field. As examples, a gender analysis process may be applied to a gender field, a first name analysis process may be applied to a first name field, and a birthdate analysis process may be applied to a birthdate field. Each of these examples is explained in further detail below; however, generally, these field specific data analysis processes attempt to resolve conflicts between data values for a particular field of data records associated with a common entity (e.g., a single patient ID) by evaluating the data values in view of other data values associated with the common entity, historical trends, and/or known associations between different data values (e.g., known based on medical knowledge).

First, in at least some embodiments, a gender specific analysis process may analyze conflicting data values (conflicting gender values) by cross referencing a first name field of the common entity and analyzing the gender value in view of the first name of the common entity. More specifically, the analysis process may retrieve and/or review social security administration (SSA) records that provide a count of first names for a particular gender for a particular period of time (e.g., a year or span of years). Then, the analysis process may determine (e.g., calculate) the odds or frequency of a certain name being a specific gender. If the frequency satisfies a certainty threshold (e.g., 60% chance of a name being a specific gender), the specific gender (e.g., male or female) may be designated as the consensus value.

Second, the field specific analysis processes for a first name field may determine a consensus value for the first name field in a similar manner. However, instead of analyzing SSA records to determine the frequency with which a person with a particular first name is a particular gender, the analysis may analyze the SSA records to attempt to determine a likely first name (from the conflicting first name values included in the records) based on a known gender and birth date. If the analysis of the SSA records (based on the gender and birthdate) indicates that a particular data value of the conflicting data values for the first name is likely to be the correct first name of the common entity (e.g., the frequency with which the first name associated with the known gender and birthdate exceeds a threshold frequency), the particular data value (e.g., the particular first name) may be designated as the consensus value. For example, if data values for the first name field include John and Joan while the gender field indicates male and the birthdate indicates 1980, SSA records from 1980 may be analyzed to determine the likelihood of males being named John and Joan in 1980. If this analysis shows a high number of babies name John and virtually zero named Joan, John may satisfy the frequency threshold and the consensus value may be designated as John.

Third, the field specific analysis processes for a birthdate field may also determine a consensus value for the birthdate field in a similar manner to the two aforementioned field specific data analysis processes. More specifically, the birthdate specific analysis process may analyze SSA records to determine frequencies of gender and first names for particular years. Based on these frequencies, the odds of a person with a specific name having a certain birthdate may be determined. If the odds associated with one data entry exceed the odds of the other conflicting entries by a certain threshold and/or if the odds of one particular data entry exceed a predetermined frequency threshold, the data entry may be designated as the consensus value.

As a more specific example, if two data records associated with a common patient ID both have data values of "Dylan" for the name field and "male" for the gender field, but include the data values 1901 and 1991 for the "birthdate" field, the frequency with which males were named Dylan in 1901 can be compared to the frequency with which males were named Dylan in 1991. Since Dylan was an extremely rare name for babies born in 1901, but extremely popular name for babies born in 1991, the odds of 1991 being the correct entry are exponentially higher than the odds of 1901 being the correct entry and, thus, 1991 may be designated as the consensus value (since the comparative odds may satisfy a predetermined threshold).

In some embodiments, a consensus value may be determined for any of the aforementioned field specific data analysis processes by analyzing all of the available data in the SSA files (e.g., data for every available year). However, in other embodiments, the field-specific analysis processes may focus on a specific subset of data from the SSA records. For example, the gender specific analysis process may focus on a particular year or range of years that is relevant to the particular data record (e.g., based on a birthdate indicated in the patient record). As a more specific example, if the gender specific data analysis process is utilized to resolve conflicting gender values for a set of matching records with the first name "Shawn" and a birth year of 1992 (e.g., two records associated with a patient ID have a value of male and two other records for the patient ID have a value of female), the data analysis may retrieve SSA files from a range of years proximate 1992 (e.g., 1992±3 years) and determine the odds of a person named Shawn being a male in that time span. If this analysis indicates that a Shawn born between 1989 and 1995 is 85% likely to be a male and the threshold is set at 60%, the consensus value may be designated as "male" (since 85% exceeds the 60% threshold). By comparison, in other embodiments, every year covered by the SSA files (e.g., inception of SSA records to present) may be analyzed to determine how likely Shawn is to be a male.

Additionally or alternatively, any of the field specific data analysis processes may attempt to resolve conflicting data values associated with a common entity by evaluating the conflicting data in view of any additional fields, known medical knowledge and/or historical trends. Put another way, additional statistical considerations may be incorporated into the field specific data analysis processes. As an example, the field specific data analysis processes may attempt to resolve conflicting data in view of gender-correlated diagnoses (e.g. prostate cancer is highly indicative of males), gender-correlated procedures (e.g. child birth is very indicative of females), gender-correlated lab test results, and gender-correlated measurements (e.g. height and weight could indicate one gender more than another).

FIG. 9 illustrates these techniques in a procedural flowchart 900. Initially, at a step 910, an ordered sequence of data analysis processes is assigned to a corresponding data field of a plurality of data objects associated with a common entity. For example, an ordered sequence of data analysis processes may be assigned to data from a particular field 730 of any records 720 associated with a common patient 710. The order assigned at step 910 may depend on the particular field being evaluated and may be assigned based on a series of rules or predefined correlations. For example, a field 730 for a patient's first name may be associated with a particular order of data analysis processes and, thus, the particular order may be assigned to a field 730 when the field 730 is determined to be a field 730 for a patient's first name.

At step 920, the data analysis processes are successively executed in the ordered sequence until a consensus value is determined for the corresponding data field. As mentioned, generally, the priority order prioritizes data analysis processes that are most likely to accurately resolve conflicts (without overriding rare occurrences). Thus, if a particular data analysis process resolves a conflict (by determining a consensus value), there is often no need to continue through the priority order. This may improve processing speed by allowing the techniques to move from conflict to conflict relatively quickly, especially when the conflicts are fairly obvious typographical errors that can be quickly resolved with the highest priority data analysis process for that particular field (e.g., the data analysis process most likely to accurately generate a consensus value for that particular field).

As an example, in at least one embodiment, a "single records priority order" or a "lists priority order" may be assigned to specific fields of records associated with a common entity (e.g., fields of two demographic records associated with a common patient ID). The single records priority order is appropriate for data fields that are only expected to include a single value, such as first name, middle name, last name, other name, marital status, preferred language, religion, death date, is deceased, opted in, opted out, consent date, email, preferred contact method, provider ID, is military veteran, is test patient, deleted from source, state, postal code, and patient identifiers (e.g., social security number or enterprise master patient index). By comparison, the lists priority order is appropriate for data fields that are expected or likely to have multiple entries (e.g., a list of phone numbers), such as race, ethnicity, insurance, insurance list, address list, and phone list.

The single records priority order may have the following priority order for executing data analysis processes: (1) No Conflict; (2) Plurality; and (3) Preferred Record. Since no conflict is listed first in the priority order, the no conflict data analysis may first be performed to ensure the conflicting data is actually conflicting. If not, any data value included in the demographic records for the particular field being evaluated may be selected as the consensus value.

Once a conflict is confirmed in the conflicting data, the plurality data analysis process will be executed against the conflicting data values. As discussed above, this data analysis process will determine if one particular value is listed more than other conflicting values and, if so, is this prevalence of the particular value enough to satisfy a particular threshold. If execution of the plurality generates a consensus value, the preferred record data analysis process is not executed against the conflicting data values. However, if execution of the plurality does not generate a consensus value (e.g., if the conflicting data values include two instances of two different data values), the preferred record data analysis process is executed against the conflicting data. As discussed above, this data analysis process determines a preferred record and generates the consensus value based on the data value included in the preferred record.

By comparison, the "lists priority order" may have the following priority order for executing data analysis processes: (1) No Conflict; (2) Aggregate; and (3) Preferred Record. Thus, after a conflict is confirmed by the first data analysis process, the second method may aggregate any data values into a single data entry to generate the consensus value. Since the aggregate data analysis process is unlikely to fail, the preferred record data analysis process may only be relevant for a null or empty list.

Notably, both of the aforementioned priority orders conclude with a preferred record data analysis process. In these instances, this allows other data analysis processes that are more likely to provide an accurate consensus value to be executed first. For example, in many instances, a data conflict will only need to resolve a single typographical error. Consequently, the plurality method is likely to accurately identify typographical errors. Moreover, in at least some embodiments, a preferred record may be designated by default to ensure that a consensus value is always found if the techniques proceed to this step (and the designation may be user configurable). In other embodiments, the "newest data analysis process" may be appended to the end of the priority order list to further ensure that a consensus value is generated.

Additionally or alternatively, field-specific priority orders, such as a gender priority order and a birthdate priority order, may be assigned to specific fields. For example, the following priority order may be assigned to a gender field: (1) No Conflict; (2) Plurality (since if all but one indicate male, female is likely a typo); (3) Gender Specific Data Analysis (try to determine a consensus value based on SSA records); (4) Preferred Record. Meanwhile, the following priority order may be assigned to a birthdate field: (1) No Conflict; (2) Plurality; (3) Birthdate Specific Data Analysis; (4) Preferred Record.

Still referring to FIG. 9, at step 930, a new record is generated with the consensuses values generated for each data field to represent the plurality of data objects. The new record resolves any conflicting data objects, but also leaves an indication of how the conflicts were resolved for tracking and/or debugging. In particular, the new record includes, for each field, a consensus value and an indication of the data analysis process used to determine the consensus value. In some embodiments, the new record may also indicate the source records that were involved in generating the consensus value (e.g., any source that included a record for that field and/or the sources of the record used to determine the consensus value). The indications of the source records and the data analysis process used to determine the consensus value preserve data lineage to allow a trace back of how the new record was created.

The new record generated at step 930 may also include a special flag or indicator to indicate that the new record is a consensus record. Since consensus records are determined with as accurate of a method as possible and resolve any conflicts, consensus records typically have higher data quality than the source records (or equal data quality if the source data record did not include any errors). Consequently, the flag or indicator may serve to indicate that the new record is a high data quality record. In subsequent analytical processing, these high quality records may be preferred to other possible data records and, thus, the new records may improve subsequent analytical processing. For example, queries run against the source data will be less likely to return erroneous results when run against the new records since the conflict resolution has eliminated errors included in source records that would otherwise cause the records to erroneously provided in response to certain queries.

It will be appreciated that the embodiments described above and illustrated in the drawings represent only a few of the many ways of implementing embodiments for resolving conflicting data included in records associated with a common entity.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, conflict resolution module, etc.). These systems may include any types of monitors and input devices (e.g., keyboard, mouse, voice recognition, etc.) to enter and/or view information.

It is to be understood that the software (e.g., conflict resolution module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., conflict resolution module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., matched data records, new records, thresholds, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may utilize data in any desired structure (e.g., records, data objects, data structures, etc.), and associate (or disassociate) the data with any desired entity (e.g., person, corporate or other business entity, healthcare or other medical related entity, healthcare provider, etc.). The conflict resolution process may compare any quantity of records (e.g., individual records, groups of records, sets of groups, collections of sets, etc.) based on any desired criteria (e.g., any quantity or combination of record fields or features, etc.).

The present invention embodiments may employ any number of any type of user interface (e.g., Graphical User Interface (GUI), command-line, prompt, etc.) for obtaining or providing information (e.g., queries, analytic results, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for associating data from various data systems with any type of common entity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method of resolving conflicting data among data objects associated with a common entity comprising:

assigning, via at least one processor, an ordered sequence of a plurality of data analysis processes executable by the at least one processor to a corresponding data field of a plurality of data objects associated with a common entity in a repository, wherein the data objects include electronic records and the repository stores the electronic records, wherein the corresponding data field is the same data field across the plurality of data objects and at least two of the data objects include different values for the corresponding data field, wherein each data analysis process performs a different technique on the corresponding data field of the plurality of data objects to resolve conflicts between the different values for the corresponding data field, and wherein the plurality of data objects each includes a plurality of data fields and at least two of the plurality of data fields are assigned a different ordered sequence of the data analysis processes;

calling and executing, via the at least one processor, the ordered sequence of data analysis processes on the corresponding data field of the plurality of data objects to determine a consensus value from the corresponding data field of the plurality of data objects to serve as a value for the corresponding data field of each of the plurality of data objects, wherein two or more of the data analysis processes are successively executed in the ordered sequence by executing a successive data analysis process after a prior data analysis process fails to determine the consensus value for the corresponding data field, and wherein the ordered sequence includes a field specific data analysis process that determines the consensus value based on statistical information of occurrences of a combination of the corresponding data field and at least one other data field of the plurality of data objects in data from external data sources;

generating and storing, via the at least one processor, a new data object in the repository for the common entity including the consensus value for the corresponding data field of each of the plurality of data objects and an indicator to distinguish the new data object from the plurality of data objects as containing the consensus value; and processing, via the at least one processor, a query for the repository including data objects of entities by identifying the new data object based on the indicator and processing the query against the new data object including the consensus value instead of the plurality of data objects including different values to produce search results.

2. The method of claim 1, wherein one or more of the data analysis processes apply probabilistic estimates to determine the consensus value.

3. The method of claim 2, wherein the probabilistic estimates are based on frequency of co-occurrences of values of the corresponding data field across the plurality of data objects.

4. The method of claim 1, wherein the plurality of data objects includes demographic records comprising the corresponding data field, and the common entity includes a patient.

5. The method of claim 4, wherein one of the data analysis processes uses clinical information of the patient to determine a likelihood of a preference for one of the different values for the corresponding data field to be the consensus value.

6. The method of claim 1, further comprising:
storing information pertaining to the consensus value, the data analysis process of the ordered sequence determining the consensus value, and the data object containing the consensus value as a value for the corresponding data field.

7. A system for resolving conflicting data among data objects associated with a common entity comprising:
at least one processor configured to:
assign an ordered sequence of a plurality of data analysis processes executable by the at least one processor to a corresponding data field of a plurality of data objects associated with a common entity in a repository, wherein the data objects include electronic records and the repository stores the electronic records, wherein the corresponding data field is the same data field across the plurality of data objects and at least two of the data objects include different values for the corresponding data field, wherein each data analysis process performs a different technique on the corresponding data field of the plurality of data objects to resolve conflicts between the different values for the corresponding data field, and wherein the plurality of data objects each includes a plurality of data fields and at least two of the plurality of data fields are assigned a different ordered sequence of the data analysis processes;

call and execute the ordered sequence of data analysis processes on the corresponding data field of the plurality of data objects to determine a consensus value from the corresponding data field of the plurality of data objects to serve as a value for the corresponding data field of each of the plurality of data objects, wherein two or more of the data analysis processes are successively executed in the ordered sequence by executing a successive data analysis process after a prior data analysis process fails to determine the consensus value for the corresponding data field, and wherein the ordered sequence includes a field specific data analysis process that determines the consensus value based on statistical information of occurrences of a combination of the corresponding data field and at least one other data field of the plurality of data objects in data from external data sources;

generate and store a new data object in the repository for the common entity including the consensus value for the corresponding data field of each of the plurality of data objects and an indicator to distinguish the new data object from the plurality of data objects as containing the consensus value; and process a query for the repository including data objects of entities by identifying the new data object based on the indicator and processing the query against the new data object including the consensus value instead of the plurality of data objects including different values to produce search results.

8. The system of claim 7, wherein one or more of the data analysis processes apply probabilistic estimates to determine the consensus value.

9. The system of claim 8, wherein the probabilistic estimates are based on frequency of co-occurrences of values of the corresponding data field across the plurality of data objects.

10. The system of claim 7, wherein the plurality of data objects includes demographic records comprising the corresponding data field, and the common entity includes a patient.

11. The system of claim 10, wherein one of the data analysis processes uses clinical information of the patient to determine a likelihood of a preference for one of the different values for the corresponding data field to be the consensus value.

12. The system of claim 7, wherein the at least one processor is further configured to:
store information pertaining to the consensus value, the data analysis process of the ordered sequence determining the consensus value, and the data object containing the consensus value as a value for the corresponding data field.

13. A computer program product for resolving conflicting data among data objects associated with a common entity, the computer program product comprising one or more computer readable storage media collectively having program instructions embodied therewith, the program instructions executable by at least one processor to cause the at least one processor to:
assign an ordered sequence of a plurality of data analysis processes executable by the at least one processor to a corresponding data field of a plurality of data objects associated with a common entity in a repository, wherein the data objects include electronic records and the repository stores the electronic records, wherein the corresponding data field is the same data field across the plurality of data objects and at least two of the data objects include different values for the corresponding data field, wherein each data analysis process performs a different technique on the corresponding data field of the plurality of data objects to resolve conflicts between the different values for the corresponding data field, and wherein the plurality of data objects each includes a plurality of data fields and at least two of the plurality of data fields are assigned a different ordered sequence of the data analysis processes;

call and execute the ordered sequence of data analysis processes on the corresponding data field of the plurality of data objects to determine a consensus value from the corresponding data field of the plurality of data objects to serve as a value for the corresponding data field of each of the plurality of data objects, wherein two or more of the data analysis processes are successively executed in the ordered sequence by executing a successive data analysis process after a prior data analysis process fails to determine the consensus value for the corresponding data field, and wherein the ordered sequence includes a field specific data analysis process that determines the consensus value based on statistical information of occurrences of a combination of the corresponding data field and at least one other data field of the plurality of data objects in data from external data sources;

generate and store a new data object in the repository for the common entity including the consensus value for the corresponding data field of each of the plurality of data objects and an indicator to distinguish the new data object from the plurality of data objects as containing the consensus value; and process a query for the repository including data objects of entities by identifying the new data object based on the indicator and processing the query against the new data object including the consensus value instead of the plurality of data objects including different values to produce search results.

14. The computer program product of claim 13, wherein one or more of the data analysis processes apply probabilistic estimates based on frequency of co-occurrences of values of the corresponding data field across the plurality of data objects to determine the consensus value.

15. The computer program product of claim 13, wherein the plurality of data objects includes demographic records comprising the corresponding data field, and the common entity includes a patient.

16. The computer program product of claim 15, wherein one of the data analysis processes uses clinical information of the patient to determine a likelihood of a preference for one of the different values for the corresponding data field to be the consensus value.

17. The computer program product of claim 13, further comprising program instructions executable by the at least one processor to cause the at least one processor to:

store information pertaining to the consensus value, the data analysis process of the ordered sequence determining the consensus value, and the data object containing the consensus value as a value for the corresponding data field.

* * * * *